United States Patent
Mahadevan et al.

(10) Patent No.: US 7,368,589 B2
(45) Date of Patent: May 6, 2008

(54) PURIFICATION OF SILICONE CONTAINING COMPOUNDS BY SUPERCRITICAL FLUID EXTRACTION

(75) Inventors: Shivkumar Mahadevan, Orange Park, FL (US); Frank Molock, Orange Park, FL (US); Robert S. Ward, Lafayette, CA (US); Yuan Tian, Alameda, CA (US); Shanger Wang, Fairfield, CA (US); James M. Serpilio, Jr., Union City, CA (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 227 days.

(21) Appl. No.: 10/699,417

(22) Filed: Oct. 31, 2003

(65) Prior Publication Data

US 2005/0092680 A1 May 5, 2005

(51) Int. Cl.
*C07F 7/00* (2006.01)

(52) U.S. Cl. .................... 556/466; 134/1; 210/634; 264/1.1; 523/106

(58) Field of Classification Search ................ 210/634, 210/808; 264/1.1, 2.6, 85, 334; 556/465, 556/466; 523/106–108; 351/159, 160 R, 351/160 H; 525/165, 288, 293, 431; 208/311, 208/324
See application file for complete search history.

(56) References Cited

U.S. PATENT DOCUMENTS

| | | | | |
|---|---|---|---|---|
| 2,188,013 A | * | 1/1940 | Stanislaw et al. ........... 208/324 |
| 4,153,641 A | * | 5/1979 | Deichert et al. ............ 526/264 |
| 4,740,533 A | * | 4/1988 | Su et al. ..................... 523/106 |
| 4,810,756 A | * | 3/1989 | Spinelli ...................... 525/293 |
| 4,880,543 A | | 11/1989 | Khosah et al. |
| 5,019,628 A | * | 5/1991 | Spinelli ...................... 525/288 |
| 5,034,461 A | * | 7/1991 | Lai et al. .................... 525/100 |
| 5,070,215 A | * | 12/1991 | Bambury et al. ........... 556/418 |
| 5,371,147 A | * | 12/1994 | Spinelli et al. ............. 525/288 |
| 5,607,518 A | * | 3/1997 | Hoffman et al. .............. 134/31 |
| 5,760,100 A | * | 6/1998 | Nicolson et al. ........... 523/106 |
| 6,071,439 A | * | 6/2000 | Bawa et al. ................. 264/1.1 |
| 6,200,393 B1 | * | 3/2001 | Romack et al. ............... 134/10 |
| 6,367,929 B1 | * | 4/2002 | Maiden et al. .......... 351/160 H |
| 2004/0176628 A1 | * | 9/2004 | Kunzler et al. ............. 556/466 |

FOREIGN PATENT DOCUMENTS

EP 0 484 959 5/1992
WO WO 03/080713 10/2003

OTHER PUBLICATIONS

PCT International Search Report, dated Feb. 4, 2006, for PCT Int'l. Appln. No. PCT/US2004/035883.
Chlorine Engineering Corp., Ltd., "Purification to Modified Silicone Oil", Patent Abstracts of Japan, vol. 18, No. 385, Jul. 10, 1994.
Kim, Sunwook et al., "Phase behaviors and fractionation of polymer solutions in supercritical carbon dioxide", Journal of Supercritical Fluids, vol. 13. No. 1-3. Jun. 15, 1998, pp. 99-106.

* cited by examiner

*Primary Examiner*—Joseph Drodge

(57) ABSTRACT

The present invention relates to a process for the purification of silicone containing compounds via supercritical fluid extraction. Specifically, the present invention relates to a process comprising the steps of contacting at least one silicone containing compound with a supercritical fluid having a density of between about 0.2 and about 0.8 g/ml, decreasing said density so that two phases are formed a first phase comprising said at least one silicone containing compound and a second phase comprising at least one impurity and separating said second phase from said first phase.

15 Claims, No Drawings

PURIFICATION OF SILICONE CONTAINING COMPOUNDS BY SUPERCRITICAL FLUID EXTRACTION

FIELD OF THE INVENTION

The present invention relates to processes for the purification of silicone containing compounds via super critical fluid extraction.

BACKGROUND OF THE INVENTION

Various silicone containing compounds have found utility as starting materials in the production of medical devices, such as ophthalmic devices and particularly, soft contact lenses having improved permeability to oxygen. These compounds must be free of undesirable impurities to insure that suitable medical devices, and particularly ophthalmic devices may be produced. Typically the silicone containing compounds also include reactive groups which are polymerizable via free radical polymerization. These free radical reactive groups can complicate traditional purification techniques, such as distillation, requiring control of the distillation temperature to avoid gellation. In the case of high molecular weight silicone-containing compounds, e.g., molecular weights great than about 1000 Dalton, distillation is not possible due to the extremely high boiling points of the silicone containing compounds. Accordingly, there remains a need in the art for an efficient purification process for silicone containing compounds.

SUMMARY OF THE INVENTION

The present invention relates to a process comprising the steps of contacting at least one silicone containing compound with a supercritical fluid having a density of between about 0.2 and about 0.8 g/ml, decreasing said density so that two phases are formed a first phase comprising said at least one silicone containing compound and a second phase comprising at least one impurity and separating said second phase from said first phase.

DESCRIPTION OF THE INVENTION

As used herein, a "biomedical device" is any article that is designed to be used while either in or on mammalian tissues or fluid and preferably on or in human tissues or fluid. Examples of these devices include but are not limited to catheters, implants, stents, and ophthalmic devices such as intraocular lenses and contact lenses. The preferred biomedical devices are ophthalmic devices, particularly contact lenses, most particularly contact lenses made from silicone hydrogels.

As used herein, the terms "lens" and "ophthalmic device" refer to devices that reside in or on the eye. These devices can provide optical correction, wound care, drug delivery, diagnostic functionality or cosmetic enhancement or effect or a combination of these properties. The term lens includes but is not limited to soft contact lenses, hard contact lenses, intraocular lenses, overlay lenses, ocular inserts, and optical inserts.

As used herein the term "monomer" is a compound containing at least one polymerizable group and an average molecular weight of about less than 2000 Daltons, as measure via gel permeation chromatography refractive index detection. Thus, monomers include dimers and in some cases oligomers, including oligomers made from more than one monomeric unit.

The present invention relates to a process for the purification of silicone containing compounds via supercritical fluid extraction ("SCFE"). SCFE is a process by which a gas is heated, under pressure, until it becomes a supercritical fluid. The point at which a gas becomes a supercritical fluid is called the critical point. Above the critical point the supercritical fluids have diffusivities similar to those of gases and densities similar to liquids. The combination of high diffusivity and density makes supercritical fluids excellent purification media. When operated in the critical region, the temperature and pressure can be used to regulate the density, which regulates the solvating power of the selected supercritical fluid.

Suitable extraction fluids are non-reactive with the silicone containing compounds to be purified and have critical points below the range which would cause degradation of the silicone containing compound. Examples include carbon dioxide, ethane, ethylene, propane, propylene, chlorotrifluoromethane, mixtures thereof, and the like. Carbon dioxide is a preferred supercritical fluid because it has a low critical point (31° C. at 73.8 bar), is generally non-reactive with the silicone-containing compounds, non-flammable and environmentally benign.

It has been found that supercritical fluids having densities between about 0.2 and about 1 g/ml, preferably between about 0.2 and about 0.8 g/ml, and more preferably between about 0.4 and about 0.8 g/ml may be used to purify silicone containing compounds. The separation process of the present invention may be conducted in one step or zone or in multiple steps or zones, depending upon the number of impurities to be removed and the solubility parameters of the impurities as compared to the silicone containing compound. Where there are a number of impurities to be removed, or the solubility parameters of the impurities are similar to the solubility parameters of the silicone, multiple zones or separation steps, having different temperature-pressure profiles (separation profiles) may beneficially be used. For example, in one embodiment a two profile separation process may be used where the supercritical fluid in the first stage comprises a density between about 0.5 and 0.7 g/ml and a density of 0.1 g/ml to about 0.3 g/ml in the second stage. Any number of additional separation profiles may be included. Additional embodiments include processing comprising 3 or more separation profiles. Specific density ranges for processes with various numbers of separation profiles are shown in Table 1, below.

| # sep. profiles | 1st profile | 2nd profile | 3rd profile | 4th profile |
|---|---|---|---|---|
| 1 | 0.2-0.8 | — | — | — |
| 2 | 0.4-0.8 | 0.1-0.4 | — | — |
| 3 | 0.5-0.7 | 0.3-0.5 | 0.1-0.3 | — |
| 4 | 0.5-0.7 | 0.3-0.5 | 0.15-0.35 | 0.1-0.3 |

Throughout the remainder of the specification the conditions which are suitable for carbon dioxide will be described. However, those of skill in the art will recognize that other supercritical fluids can be used solely or as a co-extracting fluids. The critical points for other supercritical fluids are known in the art.

For the extractions of the present invention using carbon dioxide, the desired densities may be achieved by using critical parameters include pressures from about 1,000 psi to about 5,000 psi and temperatures greater than about 31° C., preferably from about 2,000 psi to about 3,000 psi and temperatures between about 31 and about 80° C.

Suitable SCFE extraction equipment is commercially available from Thar, Technologies. Streams of extracting solvent and the silicone-containing compound can be fed by high pressure pumps into the extraction vessel. The amount of extraction and type of impurities removed may be controlled by controlling the flow rate, use of extraction co-solvent, concentration of silicone containing compound which is treated, adsorption media in the extractor vessel, pressure and temperatures used. For a 5 liter size extraction vessel, suitable flow rates of supercritical fluid include those greater than about 50 g/min and preferably from about 100 to about 350 g/min. Appropriate flow rates for equipment of other sizes may be readily calculated by those of skill in the art.

The concentration of silicone containing compound which is introduced into the SCF extraction is generally between about 1 and about 10 weight % and preferably 3 to about 7 weight % based upon the weight of silicone containing compound and the supercritical fluid. Those of skill in the art will appreciate that the use of lower flow rates may allow concentrations of silicone containing compounds which are higher than the ranges specified above, and that lower concentrations may allow higher flow rates, while still achieving the desired amount of extraction.

Silicone containing compounds which may be purified by the process of the present invention include silicone containing monomers, macromers and prepolymers. Silicone containing compounds which also comprise at least one polymerizable group and particularly at least one free radical polymerizable group can be difficult to adequately purify by other means, but are readily purified by SCFE.

Examples of silicone containing monomers include monomers of Formulae I and II

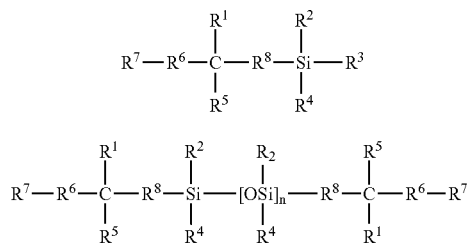

wherein:

n is an integer between 3 and 35, and preferably between 4 and 25;

$R^1$ is hydrogen, $C_{1-6}$alkyl;

$R^2, R^3$, and $R^4$, are independently, $C_{1-6}$alkyl, tri$C_{1-6}$alkylsiloxy, phenyl, naphthyl, substituted $C_{1-6}$alkyl, substituted phenyl, or substituted naphthyl where the alkyl substitutents are selected from one or more members of the group consisting of $C_{1-6}$alkoxycarbonyl, $C_{1-6}$alkyl, $C_{1-6}$alkoxy, amide, halogen, hydroxyl, carboxyl, $C_{1-6}$alkylcarbonyl and formyl, and where the aromatic substitutents are selected from one or more members of the group consisting of $C_{1-6}$alkoxycarbonyl, $C_{1-6}$alkyl, $C_{1-6}$alkoxy, amide, halogen, hydroxyl, carboxyl, $C_{1-6}$alkylcarbonyl and formyl;

$R^5$ is hydroxyl, an alkyl group containing one or more hydroxyl groups; or $(CH_2(CR^9R^{10})_yO)_x)$—$R^{11}$ wherein y is 1 to 5, preferably 1 to 3, x is an integer of 1 to 100, preferably 2 to 90 and more preferably 10 to 25; $R^9$-$R^{11}$ are independently selected from H, alkyl having up to 10 carbon atoms and alkyls having up to 10 carbon atoms substituted with at least one polar functional group, $R^6$ is a divalent group comprising up to 20 carbon atoms;

$R^7$ is a monovalent group that can under free radical and/or ionic polymerization and comprising up to 20 carbon atoms;

$R^8$ is a divalent group comprising up to 20 carbon atoms.

Reaction mixtures of the present invention may include more than one hydroxyl-functionalized silicone containing monomer.

For monofunctional hydroxyl functionalized silicone containing monomer the preferred $R^1$ is hydrogen, and the preferred $R^2, R^3$, and $R^4$, are $C_{1-6}$alkyl and tri$C_{1-6}$alkylsiloxy, most preferred methyl and trimethylsiloxy. For multifunctional (difunctional or higher) $R^1$-$R^4$ independently comprise ethylenically unsaturated polymerizable groups and more preferably comprise an acrylate, a styryl, a $C_{1-6}$alkylacrylate, acrylamide, $C_{1-6}$alkylacrylamide, N-vinyllactam, N-vinylamide, $C_{2-12}$alkenyl, $C_{2-12}$alkenylphenyl, $C_{2-12}$alkenylnaphthyl; or $C_{2-6}$alkenylphenyl$C_{1-6}$alkyl.

The preferred $R^5$ is hydroxyl, —$CH_2OH$ or —$CH_2CHOHCH_2OH$, with hydroxyl being most preferred.

The preferred $R^6$ is a divalent $C_{1-6}$alkyl, $C_{1-6}$alkyloxy, $C_{1-6}$alkyloxy$C_{1-6}$alkyl, phenylene, naphthalene, $C_{1-12}$cycloalkyl, $C_{1-6}$alkoxycarbonyl, amide, carboxy, $C_{1-6}$alkylcarbonyl, carbonyl, $C_{1-6}$alkoxy, substituted $C_{1-6}$alkyl, substituted $C_{1-6}$alkyloxy, substituted $C_{1-6}$alkyloxy$C_{1-6}$alkyl, substituted phenylene, substituted naphthalene, substituted $C_{1-12}$cycloalkyl, where the substituents are selected from one or more members of the group consisting of $C_{1-6}$alkoxycarbonyl, $C_{1-6}$alkyl, $C_{1-6}$alkoxy, amide, halogen, hydroxyl, carboxyl, $C_{1-6}$alkylcarbonyl and formyl. The particularly preferred $R^6$ is a divalent methyl (methylene).

The preferred $R^7$ comprises a free radical reactive group, such as an acrylate, a styryl, vinyl, vinyl ether, itaconate group, a $C_{1-6}$alkylacrylate, acrylamide, $C_{1-6}$alkylacrylamide, N-vinyllactam, N-vinylamide, $C_{2-12}$alkenyl, $C_{2-12}$alkenylphenyl, $C_{2-12}$alkenylnaphthyl, or $C_{2-6}$alkenylphenyl$C_{1-6}$alkyl or a cationic reactive group such as vinyl ether or epoxide groups. The particularly preferred $R^7$ is methacrylate.

The preferred $R^8$ is is a divalent $C_{1-6}$alkyl, $C_{1-6}$alkyloxy, $C_{1-6}$alkyloxy$C_{1-6}$alkyl, phenylene, naphthalene, $C_{1-12}$cycloalkyl, $C_{1-6}$alkoxycarbonyl, amide, carboxy, $C_{1-6}$alkylcarbonyl, carbonyl, $C_{1-6}$alkoxy, substituted $C_{1-6}$alkyl, substituted $C_{1-6}$alkyloxy, substituted $C_{1-6}$alkyloxy$C_{1-6}$alkyl, substituted phenylene, substituted naphthalene, substituted $C_{1-12}$cycloalkyl, where the substituents are selected from one or more members of the group consisting of $C_{1-6}$alkoxycarbonyl, $C_{1-6}$alkyl, $C_{1-6}$alkoxy, amide, halogen, hydroxyl, carboxyl, $C_{1-6}$alkylcarbonyl and formyl. The particularly preferred $R^8$ is $C_{1-6}$alkyloxy$C_{1-6}$alkyl.

Examples of hydroxyl-functionalized silicone containing monomer of Formula I that are particularly preferred are 2-propenoic acid, 2-methyl-,2-hydroxy-3-[3-[1,3,3,3-tetramethyl-1-[(trimethylsilyl)oxy]disiloxanyl]propoxy]propyl ester (which can also be named (3-methacryloxy-2-hydroxypropyloxy)propylbis(trimethylsiloxy)methylsilane)

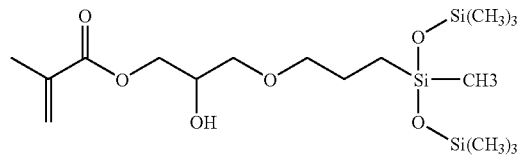

The above compound, (3-methacryloxy-2-hydroxypropyloxy)propylbis(trimethylsiloxy)methylsilane is formed from an epoxide, which produces an 80:20 mixture of the compound shown above and (2-methacryloxy-3-hydroxypropyloxy)propylbis(trimethylsiloxy)methylsilane. In some embodiments of the present invention it is preferred to have some amount of the primary hydroxyl present, preferably greater than about 10 wt % and more preferably at least about 20 wt %.

Other suitable hydroxyl-functionalized silicone containing monomers include (3-methacryloxy-2-hydroxypropyloxy)propyltris(trimethylsiloxy)silane

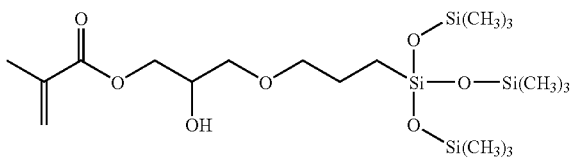

bis-3-methacryloxy-2-hydroxypropyloxypropyl polydimethylsiloxane

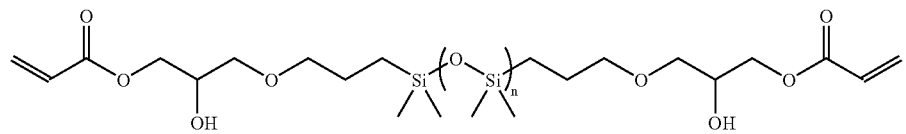

3-methacryloxy-2-(2-hydroxyethoxy)propyloxy)propylbis(trimethylsiloxy)methylsilane

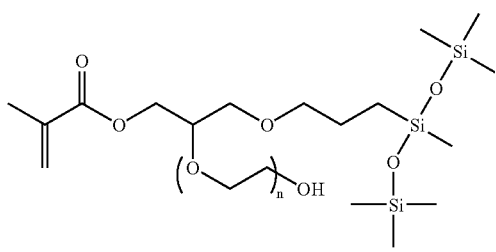

N,N,N',N'-tetrakis(3-methacryloxy-2-hydroxypropyl)-α,ω-bis-3-aminopropyl-polydimethylsiloxane The reaction products of glycidyl methacrylate with amino-functional polydimethylsiloxanes may also be used as a hydroxyl-functional silicone containing monomer. Other suitable hydroxyl-functional silicone containing monomers include those disclosed in columns 6,7 and 8 of U.S. Pat. No. 5,994,488, and monomers disclosed in U.S. Pat. Nos. 4,259,467; 4,260,725; 4,261,875; 4,649,184; 4,139,513, 4,139,692, US 2002/0016383, U.S. Pat. Nos. 4,139,513 and 4,139,692. These and any other patents or applications cited herein are incorporated by reference.

Still additional structures which may be suitable hydroxyl-functionalized silicone containing monomers include those similar to the compounds disclosed in Pro. ACS Div. Polym. Mat. Sci. Eng., Apr. 13-17, 1997, p. 42, and having the following structure:

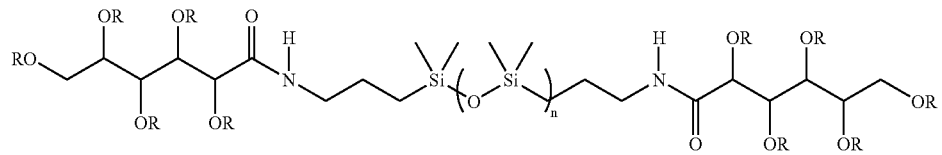

Where n=1-50 and R independently comprise H or a polymerizable unsaturated group, with at least one R comprising a polymerizable group, and at least one R, and preferably 3-8 R, comprising H.

Additional suitable hydroxyl-functionalized silicone containing monomers are disclosed in U.S. Pat. No. 4,235,985.

Suitable multifunctional hydroxyl-functionalized silicone monomers are commercially available from Gelest, Inc, Morrisville, Pa. or may be made using the procedures disclosed in U.S. Pat. Nos. 5,994,488 and 5,962,548. Suitable PEG type hydroxyl-functionalized silicone monomers may be made using the procedures disclosed in PCT/JP02/02231.

Additional suitable siloxane containing monomers include, amide analogs of TRIS described in U.S. Pat. No. 4,711,943, vinylcarbamate or carbonate analogs described in U.S. Pat. No. 5,070,215, and monomers contained in U.S. Pat. No. 6,020,445 are useful and these aforementioned patents as well as any other patents mentioned in this specification are hereby incorporated by reference. More specifically, 3-methacryloxypropyltris(trimethylsiloxy)silane (TRIS), monomethacryloxypropyl terminated polydimethylsiloxanes, polydimethylsiloxanes, 3-methacryloxypropylbis(trimethylsiloxy)methylsilane, methacryloxypropylpentamethyl disiloxane and combinations thereof may be purified by the process of the present invention.

Suitable siloxane containing macromers have a number average molecular weight between about 5,000 and about 15,000 Daltons. Siloxane containing macromers include materials comprising at least one siloxane group, and preferably at least one dialkyl siloxane group and more preferably at least one dimethyl siloxane group. The siloxane containing macromers may include other components such as urethane groups, alkylene or alkylene oxide groups, polyoxyalkalene groups, arylene groups, alkyl esters, amide groups, carbamate groups, perfluoroalkoxy groups, isocyanate groups, combinations thereof of and the like. A preferred class of siloxane containing macromers may be formed via the polymerization of one or more siloxanes with one or more acrylic or methacrylic materials. Siloxane containing macromers may be formed via group transfer polymerization ("GTP"), free radical polymerization, condensation reactions and the like. The siloxane containing macromers may be formed in one or a series of steps depending on the components selected and using conditions known in the art. Specific siloxane containing macromers, and methods for their manufacture, include those disclosed in U.S. Pat. No. 5,760,100 as materials A-D (methacrylate functionalized, silicone-fluoroether urethanes and methacrylate functionalized, silicone urethanes), those disclosed in U.S. Pat. No. 6,367,929 (styrene functionalized prepolymers of hydroxyl functional methacrylates and silicone methacrylates), and those disclosed in U.S. Pat. No. 5,371,147 (silicone containing acrylic star copolymers and macromers) the disclosures of which are incorporated herein by reference. Preferred silicone containing acrylic star copolymers and macromers comprise between about 10 and about 45 weight % hydrophilic monomers polymerized therein and preferably between about 25 and about 45 weight %, based upon the total weight of macromer or copolymer.

Suitable siloxane containing reactive prepolymers include vinyl carbamate functionalized polydimethylsiloxane, which is further disclosed in U.S. Pat. No. 5,070,215 and urethane based prepolymers comprising alternating "hard" segments formed from the reaction of short chained diols and diisocyantes and "soft" segments formed from a relatively high molecular weight polymer, which is α,ω end-capped with two active hydrogens. Specific examples of suitable siloxane containing prepolymers, and methods for their manufacture, are disclosed in U.S. Pat. No. 5,034,461, which is incorporated herein by reference.

Preferred silicone containing compounds include monomers of Formulae I or II, and more preferably monomers of Formula I, wherein $R^1$ is hydrogen; $R^2, R^3$, and $R^4$, are independently selected from the group consisting of $C_{1-6}$alkyl and tri$C_{1-6}$alkylsiloxy;

$R^5$ is hydroxyl, —$CH_2OH$ or —$CH_2CHOHCH_2OH$, $R^6$ is a divalent $C_{1-6}$alkyl, $C_{1-6}$alkyloxy, $C_{1-6}$alkyloxy$C_{1-6}$alkyl, phenylene, naphthalene, $C_{1-12}$cycloalkyl, $C_{1-6}$alkoxycarbonyl, amide, carboxy, $C_{1-6}$alkylcarbonyl, carbonyl, $C_{1-6}$alkoxy, substituted $C_{1-6}$alkyl, substituted $C_{1-6}$alkyloxy, substituted $C_{1-6}$alkyloxy$C_{1-6}$alkyl, substituted phenylene, substituted naphthalene, substituted $C_{1-12}$cycloalkyl, where the substituents are selected from one or more members of the group consisting of $C_{1-6}$alkoxycarbonyl, $C_{1-6}$alkyl, $C_{1-6}$alkoxy, amide, halogen, hydroxyl, carboxyl, $C_{1-6}$alkylcarbonyl and formyl;

$R^7$ comprises a free radical reactive group selected from the group consisting of acrylate, styryl, vinyl, vinyl ether, itaconate group, $C_{1-6}$alkylacrylate, acrylamide, $C_{1-6}$alkylacrylamide, N-vinyllactam, N-vinylamide, $C_{2-12}$alkenyl, $C_{2-12}$alkenylphenyl, $C_{2-12}$alkenylnaphthyl and $C_{2-6}$alkenylphenyl$C_{1-6}$alkyl;

$R^8$ is selected from the group consisting of divalent $C_{1-6}$alkyl, $C_{1-6}$alkyloxy, $C_{1-6}$alkyloxy$C_{1-6}$alkyl, phenylene, naphthalene, $C_{1-12}$cycloalkyl, $C_{1-6}$alkoxycarbonyl, amide, carboxy, $C_{1-6}$alkylcarbonyl, carbonyl, $C_{1-6}$alkoxy, substituted $C_{1-6}$alkyl, substituted $C_{1-6}$alkyloxy, substituted $C_{1-6}$alkyloxy$C_{1-6}$alkyl, substituted phenylene, substituted naphthalene, substituted $C_{1-12}$cycloalkyl, where the substituents are selected from one or more members of the group consisting of $C_{1-6}$alkoxycarbonyl, $C_{1-6}$alkyl, $C_{1-6}$alkoxy, amide, halogen, hydroxyl, carboxyl, $C_{1-6}$alkylcarbonyl and formyl.

Yet another preferred group of silicone containing compounds

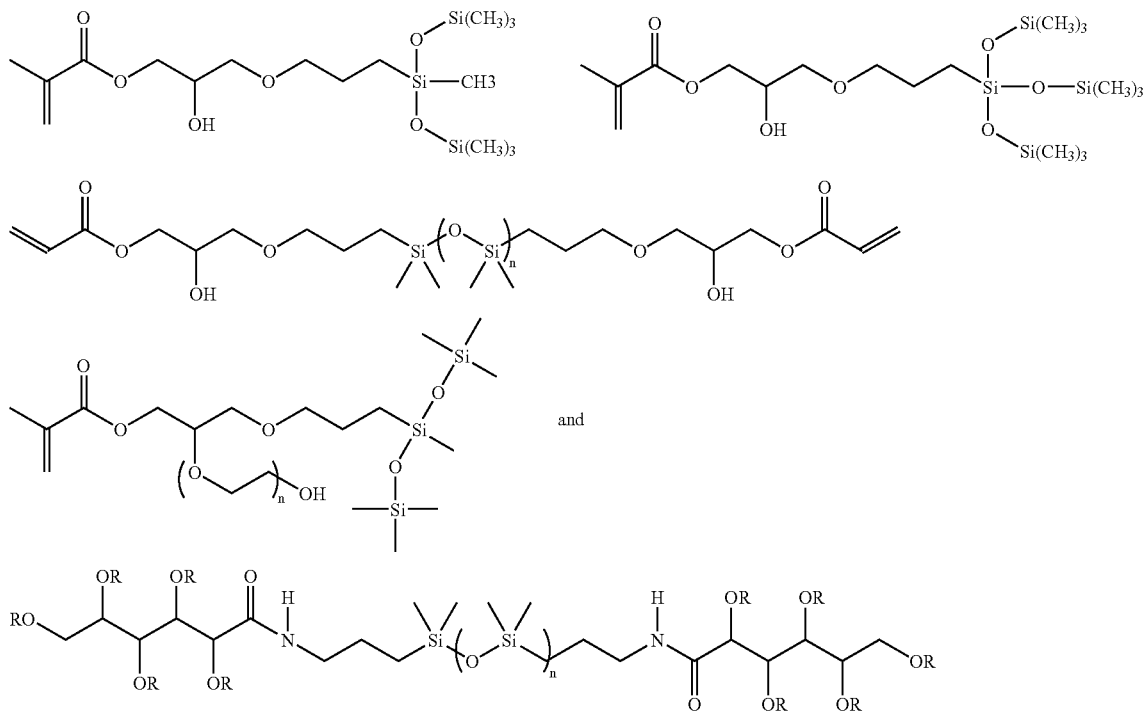

where n=1-50 and R is independently selected from H and polymerizable unsaturated group, with at least one R is a polymerizable group, and at least one R is H.

Even more preferably the silicone containing compound comprises

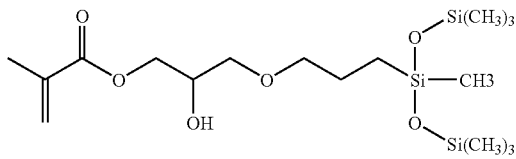

In order to illustrate the invention the following examples are included. These examples do not limit the invention. They are meant only to suggest a method of practicing the invention. Those knowledgeable in purification via supercritical fluid extraction as well as other specialties may find other methods of practicing the invention. However, those methods are deemed to be within the scope of this invention.

EXAMPLE 1

Preparation of methyl bis(trimethylsilyloxy)silylpropylglycerol mono methacrylate (SiMAA2)

A three neck, 5000 mL round bottom flask equipped with a magnetic stirrer, drying tube, and a thermocouple was charged with 92 gm (1 mole) dry lithium methacrylate. Methacrylic acid (1023 g, about 11.91 mole and containing 250 ppm MeHQ) and p-methoxyphenol (4.65 g, about 0.037 mmole) were added to the system, which was then stirred while adding glycidoxypropyl heptamethyltrisiloxane (2000 g, about 5.95 mole) to the flask. The total MeHQ content was approximately 1000 ppm by weight of the methacrylic acid used. The reaction mixture was then heated to 90° C., and consumption of the epoxide was monitored by TLC (details given below). When the reaction appeared complete by TLC, the mixture was analyzed by gas chromatography. Heating was terminated when epoxide content was <0.05% by GC/MS (conditions, column, and detector used are detailed below). The reaction was typically complete after 15 hours at 90° C.

After the system had cooled to 50° C., it was diluted with 3200 mL of hexanes, and extracted with 4×3200 mL of 0.5N aqueous NaOH, then with 2000 mL of 0.5N aqueous NaOH. The base treatments were followed up with three washes of 3200 mL of 2.5% w/v aqueous NaCl. The organics were then carefully separated from any other compounds, and dried with 250 g of sodium sulfate.

TLC Monitoring

The development solvent for this reaction mixture was 25% ethyl acetate in hexanes. The epoxide was the least polar of the compounds and had an $R_f$ of around 0.7. The visualization medium used was a mixture of the following:

| | |
|---|---|
| 1. | 10 g - vanillin |
| 2. | 10 mL - conc: $H_2SO_4$ |
| 3. | 200 mL - 95% ethyl alcohol |
| 4. | 20 drops - acetic acid |

The solution was prepared by first dissolving vanillin in 100 mL of ethyl alcohol, followed by the addition of a mixture of 100 mL ethyl alcohol $H_2SO_4$, and acetic acid.

TLC plates were dipped in the vanillin solution after developing them in the ethyl acetate/hexanes mixture. They were then heated on the glass side using either a hot plate or heat gun. Each plate was spotted three times, one with pure epoxide, one with only the reaction mixture, and the third with both the starting material and reaction mixture.

GC Method.

The purity was determined by GC as follows. A 100 uL sample of the product of this Example was dispersed into 1 mL IPA. The dispersed samples were analyzed use the instrument and conditions listed below and the purity using the equation:

| | |
|---|---|
| $P = 100\% * (A_{SiMAA2}/A_{total})$ | Where: $A_{SiMAA2}$ = area of $SiMAA_2$ peak<br>$A_{total}$ = total peak area, excluding solvent related peaks |

Instrument: GC-FID
Carrier Gas: Helium
Carrier Gas Pressure: 70 PSI
Total Flow: 75 mL/min
Septum purge: 3-5 mL/min
Hydrogen Pressure: 60 PSI
Air Pressure: 30 PSI
Detector: Flame ionization detector @ 280° C.
Inlet temperature: 280° C.
Autosampler wash solvent: isopropyl alcohol
Column: Restek RTX-5 30 m×0.25 mm×1.0 um (5% diphenyl, 95% dimethyl polysiloxane)
Injection Volume: 2 ul (100:1) split
Temperature Program:
    Initial Temperature: 60° C.
    Ramp: 10° C./min
    Final Temp: 325° C.
    Final time: 5 min
    Equilibrate: 7 min

EXAMPLE 2

SiMAA2 (44.54 gm pale yellow liquid w/strong odor), made according to Example 1 was charged to an extraction vessel (180 ml vessel), and supercritical carbon dioxide was passed through the vessel for a period of time. The high pressure stream of gas plus extracted material was then passed through a pressure reduction valve into a collector (a glass U-tube or a filter flask) to precipitate the extractables. The atmospheric gas exited the flask and passed through a meter for integration of total volume. After a desired amount of supercritical carbon dioxide was passed through the extraction vessel, the flask was removed; the pressure level was changed, and the procedure repeated twice to collect three fractions from the same initial charge. The yield and physical observation are detailed in Table 2, below. The samples were analyzed via GC and GPC analysis and the results are listed in table 2, below.

TABLE 2

| Fractn | Wt Extrct (g) | Cum. Wt (%) | Purity (HPLC) | Purity (GC) | Purity (GPC) | Observtn |
|---|---|---|---|---|---|---|
| 1 | 30.92 | 69.2 | 87.9 | 90.5 | 96.3 | water white liquid w/hint of yellow color & strong odor |

TABLE 2-continued

| Fractn | Wt Extrct (g) | Cum. Wt (%) | Purity (HPLC) | Purity (GC) | Purity (GPC) | Observtn |
|---|---|---|---|---|---|---|
| 2 | 10.21 | 92.1 | 89.1 | 91.7 | 94.9 | Very pale yellow liquid w/strong odor |
| 3 | 1.98 | 96.6 | | 17.6 | 12.3 | Yellow, odorless liquid, viscous |

The fraction 1 had a clear water like appearance with a hint of light yellow. Compared with the pale yellow color of starting material, the fraction 1 had much reduced color. The yield of fraction 1 was about 70% and GC purity was 90.5% compared with 87.6% GC purity of starting material. The GPC purity was increased from 91.8% of the starting material to 96.3% in fraction 1. Fraction 2 also showed improved purity with much reduced epoxide residual. Fraction 3 was also analyzed by GC and GPC, which indicated that the high molecular weight impurities were significantly enriched in the final fraction 3. These results suggested that SFE technique selectively extracted SiMAA2 and separated from the high molecular impurity and colored impurity with reasonable good yield, e.g., 92.1% for the combined fraction of 1 and 2. As a result, the HPLC purity of SiMAA2 was increased from 85.2% to 87.9% in fraction 1 and 89.1% in fraction 2, much of increase due to the removal of high molecular impurities.

EXAMPLE 3

The dried hexane solution of the SiMAA from Example 1 was filtered to remove all the sodium sulfate, and then added to 800 g of flash grade silica gel. The mixture was agitated for three hours at room temperature, and filtered over a fritted glass funnel to separate the organics from the silica gel. The filtrate was concentrated on a rotary evaporator at 55° C. to give the desired product.

The typical yield of product at this point was greater than 75% of the theoretical amount, and the material was >87% pure by GC and about 85% pure by HPLC, with less than 0.1% epoxide present.

Extensive slurry treatment of the SiMAA2 provided a HPLC purity of about 90% and residual epoxide of about 0.05%. Clearly the SCFE of the present invention provides significant improvements in SiMAA2 purity and extraction of specific compound such as epoxide.

EXAMPLE 4

The SiMAA2 made according to Example 1 was treated via supercritical fluid extraction using carbon dioxide as the supercritical fluid, a SFE 2x5LF from Thar, Technologies, a flow rate of 150 gm/min, a SiMAA2 concentration of 5% and the conditions listed in Table 3, below. The equipment had an extractor and three cyclone separators connected in series. The purity of each fraction collected from each extractor and cyclone was analyzed via HPLC, GC and for the concentration of starting epoxide and trimethyl silylated (TMS) SiMAA2. The results are shown in Table 3, below.

TABLE 3

| Zone | P(bar) | T(° C.) | HPLC | GC | EPX (GC) | TMS-SiMAA2 (GPC) |
|---|---|---|---|---|---|---|
| Extractor | 200 | 40 | 76.7 | 74.2 | 16.7 | 2.7 |
| Cyclone Sep. 1 | 150 | 40 | 76.6 | 74.5 | 16.9 | 2.8 |
| Cylcone Sep. 2 | 100 | 40 | 76.4 | 75.6 | 16.3 | 2.7 |
| Cyclone Sep 3 | 70 | 40 | 76.5 | 72.2 | 18.9 | 2.7 |

The purity for the starting material was 75.5 and 73.0 for HPLC and GC, respectively. The concentrations of the epoxide and trimethyl silylated SiMAA2 (TMS-SiMAA2) impurities in the starting material were 17.7 and 2.7%, respectively. These conditions were insufficient to provide separation of the product from its impurities.

EXAMPLE 5

Example 4 was repeated, except that the temperature-pressure profiles for each of the zones was varied as shown in Table 4, below. The purity of each fraction removed from each step was analyzed via HPLC, GC and for the concentration of starting epoxide and TMS SiMAA2 and is shown in Table 4, below.

TABLE 4

| Zone | P(bar) | T(° C.) | HPLC | GC | GPC | EPX (GC) | TMS-SiMAA2 (GC) | Glycol GC | HMW GPC |
|---|---|---|---|---|---|---|---|---|---|
| Ext | 130 | 60 | 69.8 | 85.7 | 68.0 | 0.15 | 0.96 | 1.82 | 31.6 |
| CS. 1 | 100 | 35 | 87.6 | 91.1 | 92.8 | 0.13 | 1.2 | 0.92 | 6.8 |
| CS. 2 | 60 | 35 | 88.1 | 90.8 | 91.7 | 0.18 | 1.2 | 0.89 | 7.4 |
| CS. 3 | 45 | 35 | 23.1 | 88.3 | 87.8 | 2.5 | 1.23 | 0.89 | 8.2 |

The purity for the starting material was 84.7, 90.1 and 87 for HPLC, GC and GPC, respectively. The concentrations of the diol, TMS-SiMAA2 and the high molecular weight impurities in the starting material were 1.0, 1.2 and 12.2%, respectively.

EXAMPLE 6

Example 4 was repeated, except that approximately 300 g of flash grade silica gel (60 angstrom pore size; 32-63 micron particle size) was placed in a perforated metal basket and placed inside the extractor column and the temperature-pressure profiles for each of the zones was varied as shown in Table 5, below. The purity of each fraction removed from each step was analyzed via HPLC, GC for the concentrations of starting epoxide, trimethyl silylated SiMAA2, SiMAA2 diol, and the high molecular weight species. The results are shown in Table 5, below. The purity for the starting material was 84.7, 90.1 and 87 for HPLC, GC and GPC, respectively. The concentrations of the diol, trimethyl silylated SiMAA2 and the high molecular weight impurities in the starting material were 1.0, 1.2 and 12.2%, respectively.

TABLE 5

| Zone | P(bar) | T(° C.) | HPLC | GC | GPC | EPX (GC) | TMS-SiMAA2 (GC) | HMW (GPC) |
|---|---|---|---|---|---|---|---|---|
| E | 155 | 70 | NA | NA | NA | NA | NA | NA |
| CS 1 | 145 | 70 | 92.5 | 92 | 97.2 | 0.08 | 0.29 | 1.5 |
| CS. 2 | 100 | 70 | 93 | 90.9 | 98.2 | 0.09 | 0.22 | 1.3 |
| CS. 3 | 50 | 70 | 88.6 | 88.7 | 97.1 | 0.25 | 0.29 | 1.2 |

These conditions led to a greatly improved purity of the SiMAA2 with significant decreases in the impurity by-products. Removal of the high molecular weight species is particularly efficient, with their concentrations being reduced by an order of magnitude. The use of silica gel greatly enhances the removal of the SiMAA2 diol.

EXAMPLE 7

Example 6 was repeated, except that the temperature-pressure profiles for each of the zones was varied as shown in Table 6, below and reduced amount of silica gel (100 gram) was used. The purity of each fraction removed from each step was analyzed via HPLC, GC and for the concentration of starting epoxide, TMS SiMAA2, diol, and high molecular weight species and is shown in Table 6, below. The purity for the starting material was 84.7, 87 and 87 for HPLC, GC and GPC, respectively. The concentrations of SiMAA2 diol, trimethyl silylated SiMAA2 and the high molecular weight impurities in the starting material were 0.99, 1.2 and 12.2, respectively.

TABLE 6

| Zone | P(bar) | T(° C.) | HPLC | GC | GPC | EPX (GC) | TMS-SiMAA2 (GC) | Glycol (GC) | HMW (GPC) |
|---|---|---|---|---|---|---|---|---|---|
| Ext | 160 | 70 | NA | NA | NA | NA | NA | NA | NA |
| CS. 1 | 155 | 70 | 89.3 | 91.1 | 95.5 | 0.1 | 1.35 | 0.53 | 7.5 |
| CS. 2 | 90 | 40 | 87.5 | 90.8 | 92.2 | 0.1 | 1.4 | 0.57 | 7.8 |
| CS. 3 | 45 | 40 | 87.8 | 90.6 | 94.5 | 0.11 | 1.52 | 0.6 | 5.5 |

EXAMPLE 8

Example 6 was repeated, except that the temperature-pressure profiles for each of the zones was varied as shown in Table 7, below. The purity of each fraction removed from each step was analyzed via HPLC, GC and for the concentration of starting epoxide and TMS-SiMAA2 and high molecular weight species is shown in Table 8, below. The purity for the starting material was 84.6, 90.1 and 87 for HPLC, GC and GPC, respectively. The concentrations of compound three and the high molecular weight impurities in the starting material were 1.2 and 12.2, respectively.

TABLE 7

| Zone | P(bar) | T(° C.) | HPLC | GC | GPC | EPX (GC) | TMS-SiMAA2 (GC) | Glycol GC | HMW GPC |
|---|---|---|---|---|---|---|---|---|---|
| Ext. | 130 | 60 | NA | NA | NA | NA | NA | NA | NA |
| CS. 1 | 95 | 40 | none | none | none | None | None | none | None |
| CS. 2 | 80 | 40 | 90.2 | 89.3 | 95.8 | 0.12 | 1.8 | 0.72 | 3.7 |
| CS. 3 | 40 | 40 | 87.9 | 88.4 | 96.9 | 0.26 | 2 | 0.78 | 2.4 |

EXAMPLE 9

Example 7 was repeated, except that the temperature-pressure profiles for each of the zones was varied as shown in Table 8, below. The purity of each fraction removed from each step was analyzed via HPLC, GC and for the concentration of starting epoxide and high molecular weight species (HMW) and is shown in Table 8, below. The purity for the starting material was 84.7, 90 and 87 for HPLC, GC and GPC, respectively. The concentrations of epoxide, trimethyl silylated SiMAA2, SiMAA2 diol and the high molecular weight impurities in the starting material were 0.14, 1.2, 1.0 and 12.2, respectively.

TABLE 8

| Zone  | P(bar) | T(° C.) | HPLC | GC   | GPC  | EPX (GC) | TMS-SiMAA2 (GC) | SiMAA2 diol (GC) | HMW GPC |
|-------|--------|---------|------|------|------|----------|-----------------|------------------|---------|
| Ext   | 130    | 60      | NA   | NA   | NA   | NA       | NA              | NA               | NA      |
| CS 1  | 100    | 40      | 94.6 | 92.3 | 95.6 | 0        | 1.1             | 0.45             | 4       |
| CS. 2 | 92     | 40      | 92.6 | 92.1 | 96.1 | 0.1      | 1.2             | 0.45             | 3.4     |
| CS. 3 | 45     | 40      | 91.4 | 91.4 | 95.6 | 0.1      | 1.4             | 0.51             | 3.4     |

EXAMPLE 10

Example 7 was repeated, except that the temperature-pressure profiles for each of the zones was varied as shown in Table 9, below. The purity of each fraction removed from each step was analyzed via HPLC, GC and for the concentration of starting epoxide, TMS SiMAA2, SiMAA2 diol and high molecular weight species (HMW) and is shown in Table 9, below. The purity for the starting material was 85, 90 and 87 for HPLC, GC and GPC, respectively. The concentrations epoxide, TMS SiMAA2, SiMAA2 diol, and the high molecular weight impurities in the starting material were 0.1, 1.2, 1.0 and 12.2, respectively.

TABLE 9

| Zone  | P(bar) | T(° C.) | HPLC | GC   | GPC  | EPX (GC) | TMS SiMAA2 (GC) | SiMAA2 diol (GC) | HMW GPC |
|-------|--------|---------|------|------|------|----------|-----------------|------------------|---------|
| Ext   | 130    | 60      | NA   | NA   | NA   |          | NA              | NA               | NA      |
| CS. 1 | 92     | 40      | 89.2 | 90.8 | 94.4 | 0.1      | 1.41            | 0.58             | 5.2     |
| CS. 2 | 80     | 40      | 89.3 | 91   | 93.7 | 0.1      | 1.36            | 0.6              | 5.8     |
| CS. 3 | 45     | 40      | 91.1 | 98.8 | 97   | 0.2      | 1.78            | 0.61             | 2.4     |

An increase in SiMAA2 purity is achieved under these conditions using supercritical carbon dioxide as the extraction medium. The concentration of the diol and high molecular weight components were also reduced. In this example, the separation conditions were not sufficient for reducing the concentrations of starting epoxide or TMS SiMAA2.

We claim:

1. A process for purifying at least one silicone containing monomer comprising the steps of contacting said at least one silicone containing monomer of Formula I or II

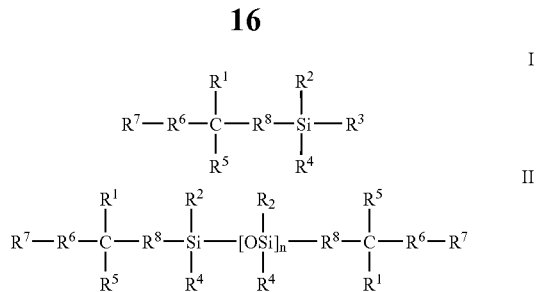

wherein:

n is an integer between 3 and 35, $R^1$ is hydrogen, $C_{1-6}$alkyl;

$R^2$, $R^3$, and $R^4$, are independently, $C_{1-6}$alkyl, $triC_{1-6}$alkylsiloxy, phenyl, naphthyl, substituted $C_{1-6}$alkyl, substituted phenyl, or substituted naphthyl where the alkyl substitutents are selected from one or more members of the group consisting of $C_{1-6}$alkoxycarbonyl, $C_{1-6}$alkyl, $C_{1-6}$alkoxy, amide, halogen, hydroxyl, carboxyl, $C_{1-6}$alkylcarbonyl and formyl, and where the aromatic substitutents are selected from one or more members of the group consisting of $C_{1-6}$alkoxycarbonyl, $C_{1-6}$alkyl, $C_{1-6}$alkoxy, amide, halogen, hydroxyl, carboxyl, $C_{1-6}$alkylcarbonyl and formyl;

$R^5$ is hydroxyl, an alkyl group containing one or more hydroxyl groups; or $(CH_2(CR^9R^{10})_yO)_x)-R^{11}$ wherein y is 1 to 5, x is an integer of 1 to 100; $R^9$-$R^{11}$ are independently selected from H, alkyl having up to 10 carbon atoms and alkyls having up to 10 carbon atoms substituted with at least one polar functional group, $R^6$ is a divalent group comprising up to 20 carbon atoms;

$R^7$ is a monovalent group that can undergo free radical and/or ionic polymerization and comprising up to 20 carbon atoms;

$R^8$ is a divalent group comprising up to 20 carbon atoms with a supercritical fluid having a density of between about 0.2 and about 1 g/ml, decreasing said density so that two phases are formed a first phase comprising said at least one silicone containing monomer and a second phase comprising at least one impurity and separating said second phase from said first phase.

2. The process of claim 1 wherein said supercritical fluid is selected from the group consisting of carbon dioxide, ethane, ethylene, propane, propylene, chlorotrifluoromethane and mixtures thereof.

3. The process of claim 1 wherein the supercritical fluid comprises carbon dioxide.

4. The process of claim 1 wherein the supercritical fluid has a density of between about 0.4 and about 0.8 g/ml.

5. The process of claim 1 wherein the contacting step comprises at least two stages a first stage and a second stage wherein the density of said supercritical fluid is lower than the density in the first stage.

6. The process of claim 5 wherein the density of the supercritical fluid in the first first stage is between about 0.4 and about 0.8 g/ml and the density of the supercritical fluid in the second stage is between about 0.1 g/ml and about 0.4 g/ml.

7. The process of claim 5 further comprising at least one additional contacting stage.

8. The process of claim 5 wherein the contacting step comprises at least three stages and the density of the supercritical fluid in the first stage is between about 0.5 and about 0.7 g/ml, the density of the supercritical fluid in the second stage is between about 0.3 g/ml and about 0.5 g/ml and the density of the supercritical fluid in a third stage is between about 0.1 g/ml and about 0.3 g/ml.

9. The process of claim 5 wherein the contacting step comprises at least four stages and the density of the supercritical fluid in the first stage is between about 0.5 and about 0.7 g/ml, the density of the supercritical fluid in the second stage is between about 0.3 g/ml and about 0.5 g/ml, the density of the supercritical fluid in a third stage is between about 0.15 g/ml and about 0.35 g/ml and the density of the supercritical fluid in a fourth stage is between about 0.1 g/ml and about 0.3 g/ml.

10. The process of claim 1 wherein said contacting step is conducted under conditions comprising pressures from about 1,000 psi to about 5,000 psi and temperatures greater than about 31° C.

11. The process of claim 1 wherein said contacting step is conducted under conditions comprising pressures from about 2,000 psi to about 3,000 psi and temperatures between about 31 and about 80° C.

12. The process of claim 1 wherein the silicone containing monomer comprises at least one polymerizable group.

13. The process of claim 1 wherein $R^1$ is hydrogen; $R^2, R^3$, and $R^4$, are independently selected from the group consisting of $C_{1-6}$alkyl and tri$C_{1-6}$alkylsiloxy;

$R^5$ is hydroxyl, —$CH_2OH$ or —$CH_2CHOHCH_2OH$, $R^6$ is a divalent $C_{1-6}$alkyl, $C_{1-6}$alkyloxy, $C_{1-6}$alkyloxy$C_{1-6}$alkyl, phenylene, naphthalene, $C_{1-12}$cycloalkyl, $C_{1-6}$alkoxycarbonyl, amide, carboxy, $C_{1-6}$alkylcarbonyl, carbonyl, $C_{1-6}$alkoxy, substituted $C_{1-6}$alkyl, substituted $C_{1-6}$alkyloxy, substituted $C_{1-6}$alkyloxy$C_{1-6}$alkyl, substituted phenylene, substituted naphthalene, substituted $C_{1-12}$cycloalkyl, where the substituents are selected from one or more members of the group consisting of $C_{1-6}$alkoxycarbonyl, $C_{1-6}$alkyl, $C_{1-6}$alkoxy, amide, halogen, hydroxyl, carboxyl, $C_{1-6}$alkylcarbonyl and formyl;

$R^7$ comprises a free radical reactive group selected from the group consisting of acrylate, styryl, vinyl, vinyl ether, itaconate group, $C_{1-6}$alkylacrylate, acrylamide, $C_{1-6}$alkylacrylamide, N-vinyllactam, N-vinylamide, $C_{2-12}$alkenyl, $C_{2-12}$alkenylphenyl, $C_{2-12}$alkenylnaphthyl and $C_{2-6}$alkenylphenyl$C_{1-6}$alkyl;

$R^8$ is selected from the group consisting of divalent $C_{1-6}$alkyl, $C_{1-6}$alkyloxy, $C_{1-6}$alkyloxy$C_{1-6}$alkyl, phenylene, naphthalene, $C_{1-12}$cycloalkyl, $C_{1-6}$alkoxycarbonyl, amide, carboxy, $C_{1-6}$alkylcarbonyl, carbonyl, $C_{1-6}$alkoxy, substituted $C_{1-6}$alkyl, substituted $C_{1-6}$alkyloxy, substituted $C_{1-6}$alkyloxy$C_{1-6}$alkyl, substituted phenylene, substituted naphthalene, substituted $C_{1-12}$cycloalkyl, where the substituents are selected from one or more members of the group consisting of $C_{1-6}$alkoxycarbonyl, $C_{1-6}$alkyl, $C_{1-6}$alkoxy, amide, halogen, hydroxyl, carboxyl, $C_{1-6}$alkylcarbonyl and formyl.

14. The process of claim 1 wherein the silicone containing monomer is selected from the group consisting of

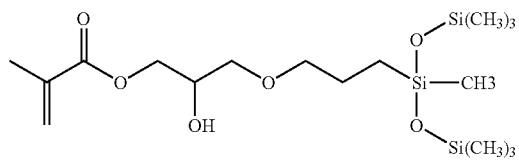
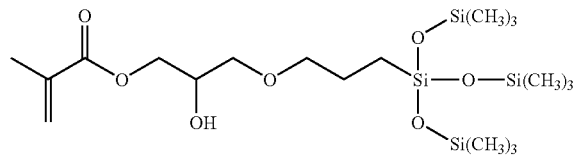

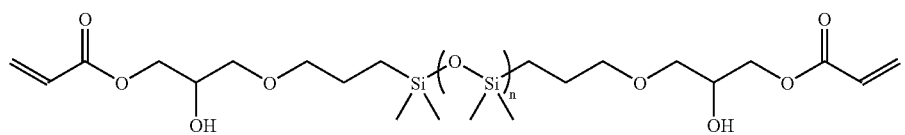

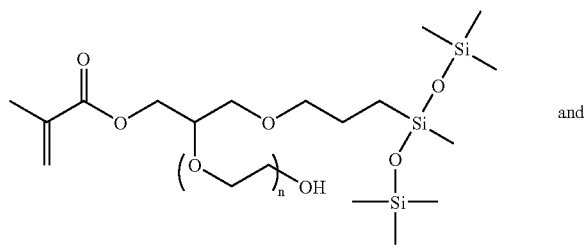

and

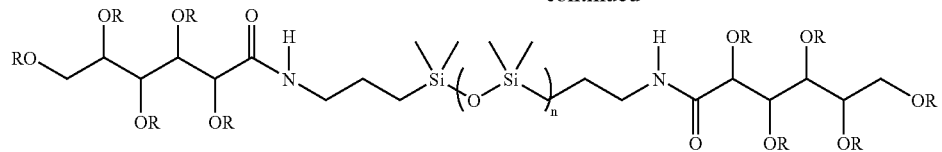
where n=1-50 and R is independently selected from H and polymerizable unsaturated group, with at least one R is a polymerizable group, and at least one R is H.
15. The process of claim 13 wherein said silicone containing monomer comprises
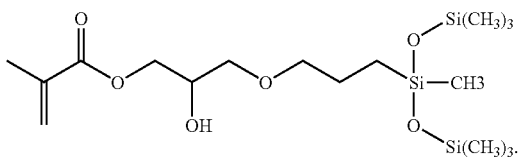
* * * * *